United States Patent [19]
Kesten et al.

[11] Patent Number: 5,423,755
[45] Date of Patent: Jun. 13, 1995

[54] CATHETER FOR PROSTATIC URETHRAL DILATATION

[75] Inventors: Randy J. Kesten; Kirsten L. Valley, both of Sunnyvale; Robert W. Reinhardt, San Jose; Jeffrey W. Krier, Montara; Sam G. Payne, Santa Clara, all of Calif.

[73] Assignee: Advanced Cardiovascular Systems, Inc., Santa Clara, Calif.

[21] Appl. No.: 934,981

[22] Filed: Aug. 26, 1992

[51] Int. Cl.⁶ .......................... A61M 29/02
[52] U.S. Cl. .................................... 604/96
[58] Field of Search .............. 604/96, 101, 103; 606/191–195; 128/4

[56] References Cited

U.S. PATENT DOCUMENTS

| | | | |
|---|---|---|---|
| 3,498,286 | 11/1970 | Polanyi et al. | 604/282 |
| 4,276,874 | 7/1981 | Wolvek et al. | 604/96 |
| 4,655,748 | 4/1987 | Mushika | 604/96 |
| 4,793,359 | 12/1988 | Sharrow | 604/96 |
| 4,820,349 | 4/1989 | Soab | 604/96 |
| 4,931,036 | 6/1990 | Kanai et al. | 604/282 |
| 4,932,958 | 6/1990 | Reddy et al. | 606/192 |
| 5,019,057 | 5/1991 | Truckai | 604/282 |
| 5,030,227 | 7/1991 | Rosenbluth et al. | 604/96 |
| 5,042,985 | 8/1991 | Elliot et al. | 604/96 |
| 5,071,429 | 12/1991 | Pinchuk et al. | 606/192 |
| 5,087,246 | 2/1992 | Smith | 604/96 |
| 5,141,518 | 8/1992 | Hess et al. | 606/194 |
| 5,159,937 | 11/1992 | Tremilis | 606/194 |
| 5,169,386 | 12/1992 | Beller et al. | 604/96 |

FOREIGN PATENT DOCUMENTS 2046096 11/1980 United Kingdom .................. 604/96

Primary Examiner—C. Fred Rosenbaum
Assistant Examiner—Manuel Mendez
Attorney, Agent, or Firm—Dykema Gossett

[57] ABSTRACT

A balloon dilatation catheter for the dilatation of a prostatic urethra having a reinforcing element extending through the elongated shaft of the catheter to prevent significant elongation or failure of the catheter and a traction member for assisting in the resistance to substantial tensile stresses. The balloon dilatation catheter also includes an expandable means between the balloon and catheter shaft to extend the length of the balloon when it is deflated. The extension of the deflated balloon prevents the balloon from bunching up and interfering with the withdrawal of the balloon through the working channel of the cystoscopic sheath upon the completion of the dilatation. The catheter has a marker for easy visualization so that the balloon can be positioned reliably and a tip construction so that the catheter can be advanced into the bladder safely.

18 Claims, 3 Drawing Sheets

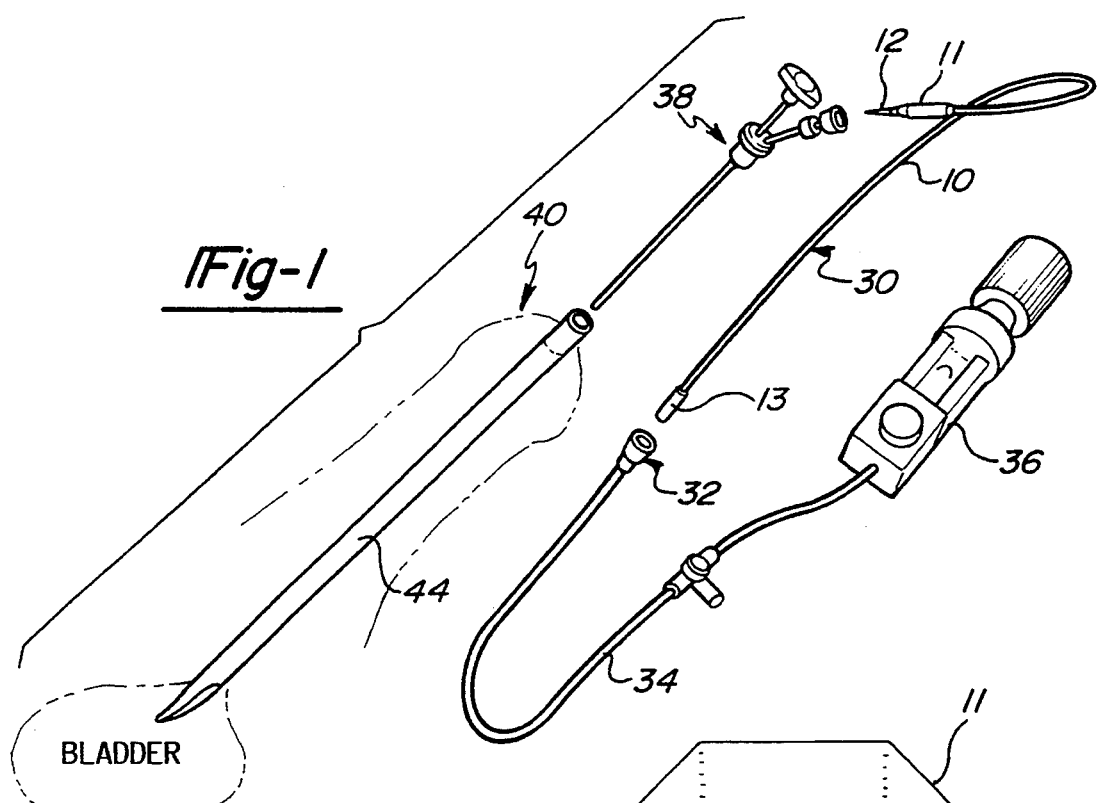
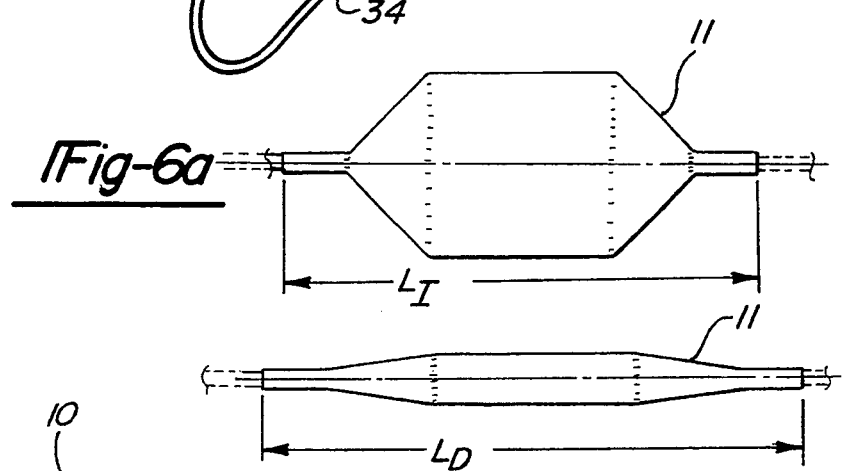
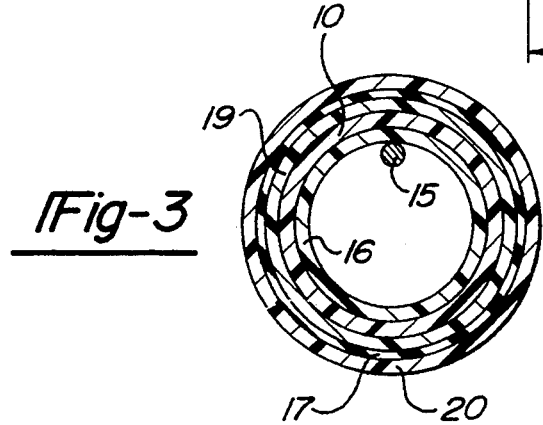
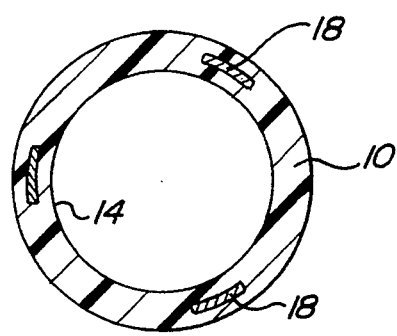

CATHETER FOR PROSTATIC URETHRAL DILATATION

This invention generally relates to a balloon dilatation catheter for the treatment of a prostatic urethra and the method of using the catheter.

BACKGROUND OF THE INVENTION

The most common use of balloon catheters to dilate body passages is angioplasty in which a balloon catheter is used to dilate a coronary artery by collapsing or compressing plaque. Another use for balloon catheters is uroplasty, which is a treatment to relieve urinary obstruction caused by the swelling of the prostate.

The dilatation of the prostatic urethra to treat urethral blockage resulting from benign prostatic hyperplasia has been considered for many years. For example, Guthry in 1830, Ciale in 1841, Mercier in 1850 and Kramer in 1910 all developed metal dilators to unblock urethral obstructions. A good description of the early work in this area can be found in Hinman, F., Jr. (Ed), *Benign Prostatic Hypertrophy*, Chapter 5, Springer-Valag, 1983. Russinovich et al. utilized a balloon dilatation catheter which was developed for angioplasty by Gruntzig et al. to successfully dilate the prostatic urethra of several male patients which had been partially occluded. (*Urologic-Radiology*, 2, 33-37, 1980).

For many years, transurethral resections have been commonly performed to remove sections of the prostate gland in order to relieve urinary obstruction at the neck of the bladder and in the prostatic urethra. Uropolasty, on the other hand, involves inserting a balloon into the prostatic urethra and inflating the balloon for a period of time to dilate the prostatic urethra and bladder neck. State of the art balloon catheters for uropolasty generally have such large profiles (transverse dimensions) that relatively large diameter cystoscopic sheaths are required for insertion of the catheter into the patient's urethra. Conventional rigid urological cystoscopes have sheaths with working channels having effective diameters of less than about 5 mm.

The collapsed or deflated balloons of commercially available prostatic balloon dilatation catheters are generally too large to be withdrawn into the working channel of a conventional rigid cystoscopic sheath. For example, it has not heretofore been commercially possible to fabricate a catheter that will fit through the working channel of a rigid cystoscope if the balloon is expanded to form a diameter of approximately 30-35 mm, which is a preferred expansion dimension for the uroplasty procedure. A large balloon size creates the difficulty that even if the non-balloon portion of the catheter body fits into the working channel of the cystoscope, it is very difficult to fold or wrap the balloon to fit through the small working channel. Thus, there has been a need for a balloon catheter in which the balloon can be folded or collapsed more compactly to reduce its deflated profile such that it will fit through the small working channel of conventional cystoscopes.

Effective dilation of the prostatic urethra also requires some means for applying considerable pressure to the urethral wall while maintaining a consistent limit on tissue distension. Further, when a balloon on a dilatation catheter is inflated to dilate a prostatic urethra, the inflated balloon has the tendency to move from the urethra into the bladder. For effective dilatation of the prostatic urethra, the dilatation catheter must be firmly grasped by the physician during the dilation in order to hold the balloon in place and prevent its migration into the bladder. The force on the balloon urging its movement results in significant tensile stresses being applied to the catheter shaft and the juncture between the balloon and the catheter shaft. These high stresses can result in significant extension or even the failure of the shaft or the juncture between the balloon and the shaft. Thus, there has been a need for a balloon catheter which is constructed in such a way that it will withstand the significant tensile stresses being applied during the uroplasty procedure.

What has been needed and heretofore been unavailable is a prostatic dilatation catheter which has sufficiently low shaft and deflated balloon profiles to allow the catheter to be withdrawn through the working channel of a conventional rigid cystoscope and which also has sufficient tensile strength to withstand the tensile stresses imposed upon the catheter during its use. The present invention satisfies these and other needs.

SUMMARY OF THE INVENTION

The present invention is directed to an improved catheter for the dilatation of prostatic urethra and to the method of using the improved catheter. More specifically, the balloon catheter of the present invention is designed to enable effective dilation of the prostatic urethra by a procedure that may be performed through and visualized by a standard urological cystoscope. Some of the elements contributing to the improved catheter construction include the type of material used in the fabrication of the balloon, the design of the fixation of the balloon ends, and the design of other stress-carrying members. Further, the design of the catheter tip and the use of a visual marker contribute to the improved processing method provided by the balloon catheter of the present invention.

The dilatation catheter of the invention generally includes an elongated catheter shaft having an inner lumen extending therein which is adapted to direct inflation fluid to the interior of an inflatable member on a distal portion of the shaft. The shaft is provided with reinforcing means secured directly or indirectly to the balloon to prevent significant extension of the shaft or failure of the juncture between the balloon and the shaft when the balloon is inflated during a prostatic dilatation procedure. The catheter shaft is substantially less than 3 mm in diameter to facilitate advancement through a conventional cystoscopic sheath, and the inflatable member has an inflatable diameter between 15 to 50 mm, with the preferable inflated diameter being about 35 mm to ensure effective dilatation of the prostatic urethra. The construction of the present invention also includes means for providing a collapsed balloon profile that is sufficiently small to enable the catheter to be withdrawn efficiently through the sheath of a conventional cystoscope.

In one embodiment, a core member made of high strength material, such as stainless steel or a superelastic alloy such as NiTi, extends through the inner lumen of the catheter shaft and is secured directly or indirectly to the balloon. The proximal end of the core member is secured to a proximal portion of the catheter shaft or to a traction member on the proximal end of the catheter shaft. The distal extremity of the core member may be secured to the catheter shaft at either the proximal or distal ends of the balloon. A short metallic hypotube is secured to the interior surface of the inner lumen of the shaft at a location where the balloon is secured to the exterior of the catheter shaft. The core member may be secured, e.g. by welding, to the hypotube. The core member provides reinforcement to the catheter shaft to enable the shaft to handle the tensile stresses imposed on the catheter from the inflation of the balloon during the dilatation procedure.

The catheter shaft is provided with means to extend the length of the balloon when it is in the deflated state to reduce the profile thereof sufficiently to facilitate the withdrawal thereof through a conventional rigid cystoscopic sheath. A suitable means to extend the balloon length includes interfitting members which are secured directly or indirectly to the balloon and with the interfitting members including biasing means to urge the ends of the balloon away from each other.

The balloon of the present invention is made from poly(ethylene)terephtalate, which is a high strength material having the appropriate mechanical properties for the uroplasty procedure and being formable to reliably inflate to a known size. The high strength of the material enables a balloon with a wall thickness in the range of 0.0007–0.0010 inch which may be inflated to a predictable size and compacted to a small profile. If the balloon is rigidly attached to the catheter shaft, the material tends to "bunch" up as it deflates to absorb the length change that occurs between the inflated and deflated states of the balloon. As set forth previously, the present construction includes means for providing axial movement which acts on the balloon material for extending and causing further compaction of the balloon profile in its deflated state. Further, the necks of the balloon are formed to a small diameter and are attached to the catheter shaft in a smooth and continuous manner. The balloon attachments include fixation wedge elements that both provide a smooth transition for the ends of the balloon and provide improved tensile strength to minimize the possibility of failures.

The present invention also includes an attachment element in the form of a traction member so that the catheter can be connected to an external fixation and balloon pressurization apparatus. The traction member provides a direct mechanical linkage between the core member and the catheter shaft. In order to permit placement through a standard rigid cystoscope, the traction member is formed by rigidly encapsulating a coined end of the core member within a plastic material.

Unlike fixed wire angioplasty catheters, the tip of the balloon catheter for uroplasty procedures is not used to "steer" the catheter through tortuous anatomy. Instead, the passage from the urethral orifice to the bladder is essentially a clear path with no branches. The present construction includes a catheter tip which presents a soft leading edge that minimizes damage to the urethra during manipulation and acts as a soft bumper for the distal end of the catheter as it is pushed against the bladder wall prior to positioning the balloon within the prostate. Another feature of the present construction is its ability to be visualized by a standard rigid cystoscope. Such visualization is particularly important during the pre-dilatation positioning of the catheter. The design of the balloon catheter of the present invention allows the catheter to fit within the limited space remaining in the cystoscope with the conventional optics in place. A visual white band marker is included on the proximal end of the balloon which may be readily identified through the cystoscope lens against the dark background of the catheter shaft. A dulled surface on the polymer material of the catheter shaft is provided for reducing glare and increasing visibility.

The catheter of the invention has a low profile that is easily advanced and withdrawn through the working channel of a conventional rigid cystoscope, and the catheter has sufficient strength in the longitudinal direction to minimize the longitudinal extension or possible failure of the shaft at the juncture between the shaft and the balloon upon the inflation of the balloon within the prostatic urethra. These and other advantages of the invention will become more apparent from the following detailed description thereof, when taken in conjunction with the accompanying exemplary drawings.

BRIEF DESCRIPTION OF THE DRAWINGS

FIG. 1 shows the balloon catheter of the present invention in relation to a cystocope and related apparatus.

FIG. 3 is a transverse cross-sectional view of the catheter shown in FIG. 2 taken along the lines 3—3.

FIG. 4 is a transverse cross-sectional view of a catheter shaft of an alternative embodiment wherein reinforcing ribbons are incorporated within the wall of the catheter shaft.

FIGS. 6A and 6B schematically illustrates the extension of a balloon upon its deflation to reduce the deflated profile thereof in accordance with an alternative embodiment of the invention.

DETAILED DESCRIPTION OF THE INVENTION

Figure 2:
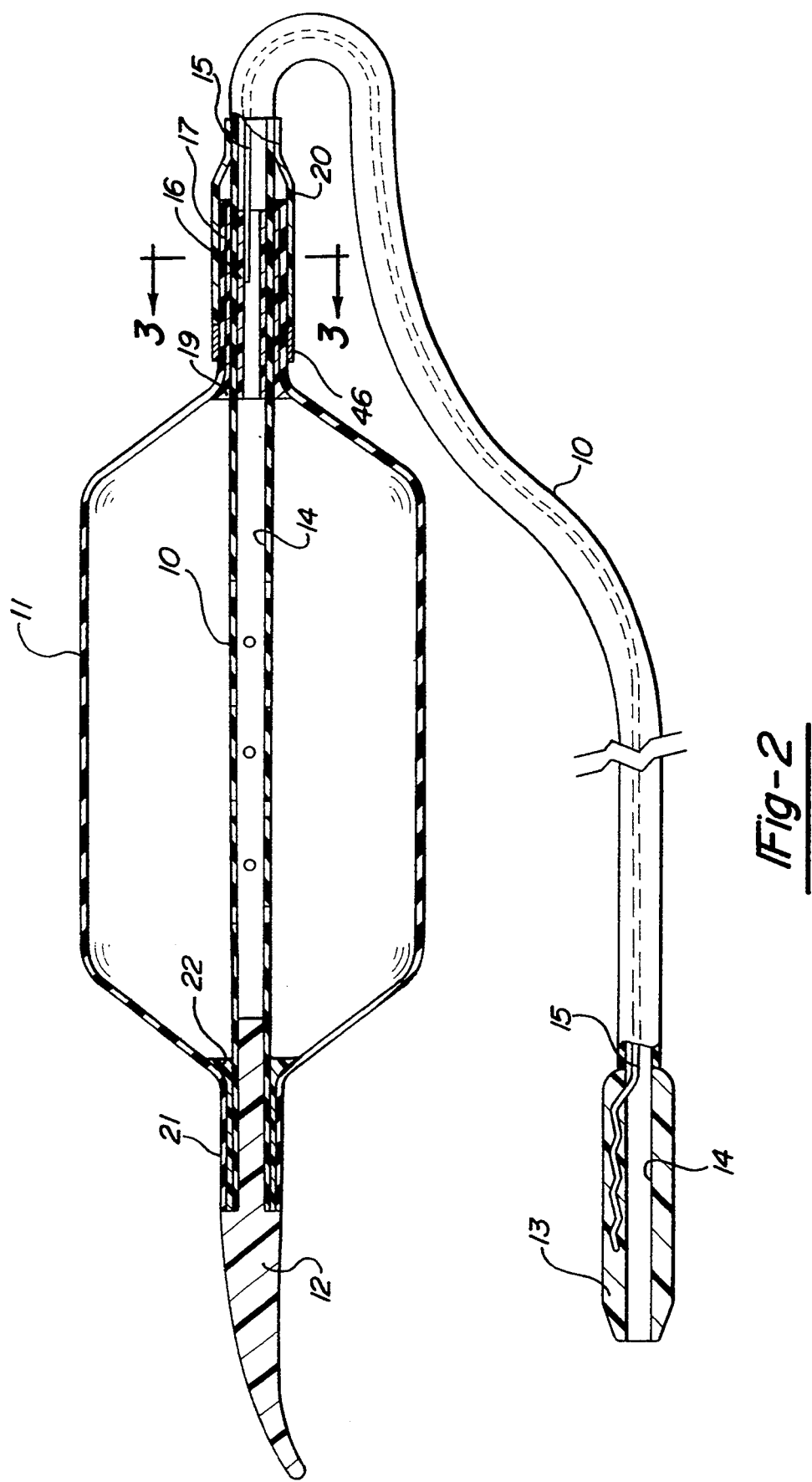
FIG. 2 is a longitudinal view, partially in section, of a dilatation catheter embodying features of the invention.

FIGS. 1 and 2 depict a balloon dilatation catheter 30 which embodies features of the invention and which is suitable for the dilatation of a prostatic urethra in a human patient. The catheter generally includes a plastic catheter shaft 10, an inflatable balloon 11 secured to a distal portion of the shaft 10, an elastomeric tip 12 which extends distal to the balloon to minimize traumatic engagement with the bladder or urethral walls, and a traction member 13 on the proximal end of the shaft.

Inner lumen 14 extends through the catheter shaft 10 and is in fluid communication with the interior of the balloon 11 through openings in the wall of shaft 10 as shown in FIG. 2. A reinforcing core member 15 is disposed within the inner lumen 14. The proximal end of the reinforcing core member 15 is coined and encapsulated within the enlarged traction member 13 and the distal end thereof is secured to a relatively short metallic hypotube 16 which is bonded to inner lumen 14 adjacent to the proximal end 17 of the balloon 11. The proximal end of the reinforcing core member may be embedded within traction member 13 or secured thereto by suitable adhesive. The distal end of the reinforcing member 15 may be secured to the hypotube 16 by welding or other suitable means. The reinforcing core member 15 is preferably formed of stainless steel wire from about 0.010 to about 0.020 inch in diameter, although other high strength materials may be employed.

FIG. 4 illustrates an alternative embodiment wherein reinforcing ribbons 18 are incorporated within the wall of the catheter shaft 10. The reinforcing ribbons 18 may likewise be formed of high strength materials such as stainless steel and generally have a rectangular shaped cross-section with a width of about 0.001 to about 0.010 inch and a thickness of about 0.001 to about 0.003 inch.

The proximal end or waist 17 of the balloon 11 is secured to the exterior of a first intermediate tubular fixation member 19 which has a flared or wedge shaped distal end as shown in FIG. 2. The intermediate tubular member 19 is secured to the exterior of the catheter shaft 10. The relatively short hypotube section 16 is secured to the interior of the catheter shaft 10. An outer bonding element 20 is secured to the exterior of the proximal waist 17 and to the shaft 10 to further secure the proximal end of the balloon to the catheter shaft 10. The distal end or waist 21 of the balloon 11 is secured to the exterior of a second intermediate tubular member 22 which has a flared proximal end. The second intermediate tubular member 22 is in turn secured to the exterior of the distal extremity of shaft 10. The intermediate tubular members 19 and 22 provide a smooth transition and minimize the possibility of failure between balloon waists 17 and 21 and shaft 10 as a result of the tensile stresses resulting from the inflation of the balloon 11. The balloon waists 17 and 21 and other catheter components should be sealingly bonded to avoid loss of inflation liquid during the period the balloon is inflated.

The proximal extremity of the elastomeric catheter tip member 12 is secured, e.g. by a suitable adhesive, within the inner lumen 14 in the distal extremity of the catheter shaft 10. The distal extremity of member 12 is shaped, e.g. curved as shown in the drawing, to facilitate the nontraumatic advancement of the catheter through the patient's urethra into the bladder. The flexible body 12 may be made from suitable plastic materials such as urethane or silastic.

The traction member 13 is adapted to be received in a Tuohy-Borst adapter 32 (FIG. 1) which is connected by a pressure line 34 to an inflation device 36. The outer diameter of member 13 should be substantially less than about 3 mm so that it can be backloaded through the bridge 38 of a conventional urological cystoscope 40.

Figure 5:
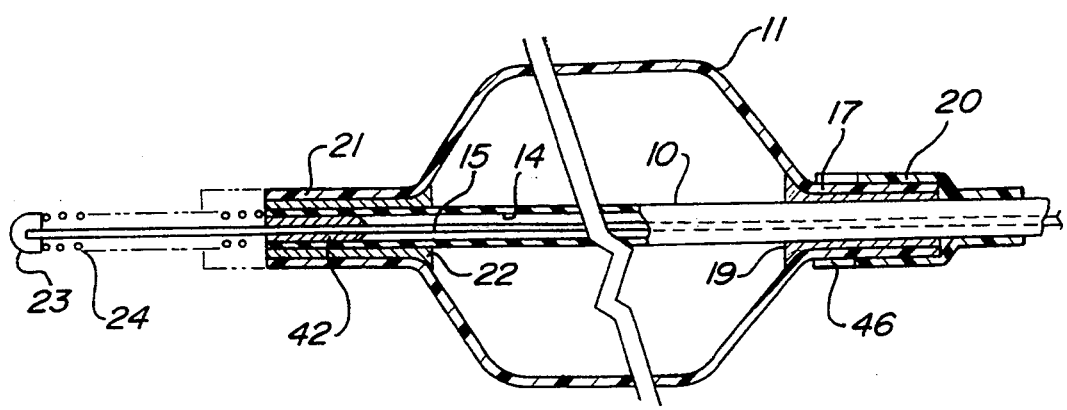
FIG. 5 is a partial longitudinal cross-sectional view of an alternative embodiment wherein the distal portion of the catheter shaft is secured to the distal end of the balloon and is provided with a flexible coil on the distal end thereof.

FIG. 5 illustrates an alternative embodiment of the invention wherein the reinforcing core member 15 extends through the interior of the balloon 11 and is secured to a plug 23 on the distal end of a coil 24. The plug 23 is soldered between the distal end of the coil 24 and the distal end of the reinforcing member 15. An intermediate member 42 is provided within the inner lumen 14 under the distal waist 21 of the balloon 11 to provide a passage and guide for core member 15 as shown in copending application Ser. No. 07/483,394, filed Feb. 14, 1990, which is hereby incorporated herein by reference in its entirety. The catheter of the alternative embodiment is otherwise as shown in FIG. 1.

The balloon 11 of the catheter must have a relatively large inflated diameter, i.e. at least about 15 to about 50 mm, in order to effectively dilate a prostatic urethra. However, when balloons of this size are deflated, they tend to bunch up because both ends are fixed to the relatively inflexible catheter shaft extending through the interior of the balloon, and therefore, a relatively large profile is presented which makes withdrawal of the balloon back into the working channel of a conventional rigid urological cystoscope difficult to accomplish. Reference is made to FIG. 6B which schematically illustrates an embodiment of the invention which involves increasing the length of the balloon 11 when the balloon is deflated so as to avoid the bunching up of the balloon and present a very low profile balloon which can be easily withdrawn into the sheath 44 of a conventional urological cystoscope 40. As shown in FIG. 6A, when the balloon is inflated the length thereof decreases.

Figure 7:
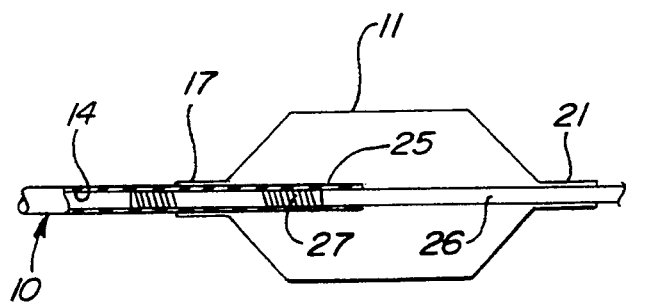
FIG. 7 is a simplified schematic drawing of a dilatation catheter having an extendable distal shaft section which allows for the extension of the length of the balloon upon the deflation thereof and the contraction of the length upon the inflation thereof as shown in FIGS. 6A and 6B.
Figure 8:
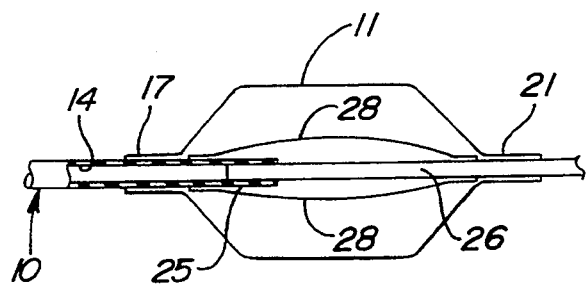
FIG. 8 is a simplified schematic drawing of an alternate embodiment to that shown in FIG. 7.

Means to accomplish the extension of the balloon length when the balloon 11 is deflated and which allows the contraction of the balloon length when the balloon is inflated are illustrated in FIGS. 7 and 8. As shown in FIG. 7 telescoping tubular portions 25 and 26 are provided which are secured to the proximal and distal waists 17 and 21 respectively of the balloon 11. A biasing means, such as spring 27, is disposed within the inner lumen 14 of the proximal tubular portion 25 to urge element 26 away and thus lengthen the balloon 11. Upon inflation of the balloon 11, the length of the balloon contracts causing the telescoping element 26 to be urged further into the portion of the inner lumen 14 within the tubular portion 25, thereby compressing spring 27. As shown in FIG. 8, the biasing means may be leaf springs 28 which have their proximal ends secured to the tubular element 25 and their distal ends secured to the telescoping element 26.

As previously discussed, the catheter shaft 10 generally has an outer diameter of less than 3 mm and preferably less than about 2 mm. It may be made from suitable plastic materials such as polyamide or polyester. The overall length of the catheter may be any convenient length but about 30 to about 80 cm has been found suitable in most instances. The balloon length may vary from about 2 to about 8 cm including the tapered necks depending upon the needs of a particular procedure. The balloon 11 has a relatively thin wall, e.g. about 0.0005 to about 0.001 inch and is preferably formed of a relatively inelastic polymer such as poly(ethylene) terephthalate. In one preferred embodiment, the shaft 10 is formed of relatively dark material, e.g. black, and is provided with a light colored, e.g. white, marker 46 at the proximal end of the balloon 11. To facilitate the low angle viewing of the marker during use with a conventional urological cystoscope, the distal dark portion of the shaft 10 is dulled to minimize the gloss which can interfere with the low angle observation of the marker.

Conventional techniques can be employed to join the various members of the catheter into the final product. Generally, bonds between plastic members may be formed by means of a suitable adhesive or, if the composition of the plastic members is appropriate, heat shrinking or heat fusion may be employed. Junctions between metallic members may be made by suitable means such as welding, brazing, soldering or adhesives.

The catheter of the invention is intended for use in procedures to treat benign prostatic hyperplasia. In a typical treatment procedure with a catheter of the invention, the physician will advance a conventional rigid cystoscope 40 into the urethra of a male patient with an obturator disposed within the cystoscopic sheath 44 until the distal end of the sheath is disposed within the patient's bladder. The obturator is replaced with a telescopic lens and a diagnostic examination is performed. The telescopic lens and bridge 38 are then removed to allow the dilatation catheter 30 of the invention to be back loaded through the bridge and then advanced through the working and channel of the cystoscope. The traction sleeve 13 on the proximal end of the catheter is mounted to the Tuohy-Borst adapter 32 which is connected by pressure line 34 to inflation device 36. The bridge of the cystoscope is remounted onto the proximal end of the cystoscopic sheath 44. The lens is then replaced to allow the visual observation of the placement of the inflatable balloon within the prostatic urethra to ensure proper placement distal to the external sphincter. Inflation fluid, e.g. saline solution, is injected through the inner lumen of the catheter to inflate the balloon. The balloon is maintained in the inflated condition at a pressure of about 2 to about 8 atmospheres, typically about 4 atmospheres, for about 5 to about 30 minutes, typically about 10 minutes. During the period when the balloon is inflated, a significant force is generated which tends to pull the balloon into the bladder. During this period the physician must maintain a firm grip on the catheter, e.g. the pressurization apparatus connected to the adapter on the proximal end of the catheter, in order to maintain the position of the inflated balloon with the prostatic urethra. Tensile forces of up to 15 pounds or more may have to be applied to the catheter shaft in order to properly maintain the position of the balloon within the urethra. After the dilatation of the prostate gland is complete, the balloon is deflated and effective dilatation is confirmed by visual observation through the lens. The bridge is removed from the sheath, the lens is removed, and the catheter is withdrawn back into the working lumen of the cystoscopic sheath. Both the catheter and the cystoscope can then be removed from the patient, or the catheter can be withdrawn from the patient through the cystoscope, leaving the cystoscope sheath in position within the patient so that the lens and bridge can be reinserted to observe the dilated urethra or so that the sheath can be advanced further into the bladder for additional observations.

The catheter of the invention allows for the direct visual placement of the balloon and the observation of the dilatation when using a conventional urological cystoscope. Moreover, with the catheter design of the invention, there is no need to interchange sheaths, guidewires and the like during the procedure and as a result there is a substantial improvement in the safety and efficiency of the procedure with the present catheter design. Various modifications and improvements can be made to the invention without departing from the scope thereof.

We claim:

1. A balloon catheter for dilating a prostatic urethra comprising:
   a) an elongated catheter shaft having an outer diameter less than or equal to 3 mm in diameter and an inner lumen therein adapted to pass inflation fluid therethrough;
   b) an inflatable member on a distal portion of the catheter shaft having an inflated diameter of at least 25 mm;
   c) means to reinforce the catheter shaft to enable the shaft to handle a tensile force of at least 10 pounds without failure;
   d) means to increase the distance between the ends of the inflatable member upon deflation thereof in order to reduce the deflated profile thereof to about 5 mm in diameter;
   e) means associated with said inflatable member for permitting easy visualization such that said inflatable member may be reliably positional;
   f) means for permitting said catheter to be conveniently advanced into a bladder;
   g) means to direct inflation fluid through the inner lumen in the catheter shaft to the interior of the inflatable member; and
   h) wherein the means to reinforce the catheter shaft is a core member secured to the catheter shaft at or near the proximal end of the inflatable member.

2. The balloon dilatation catheter of claim 1 wherein the core member is secured to the proximal end of the catheter shaft within a traction member that will fit through a bridge of a cystoscope.

3. The balloon dilatation catheter of claim 1 wherein the means to reinforce the catheter shaft is one or more elongated members disposed within the wall of the catheter shaft.

4. A catheter for dilating a prostatic urethra comprising:
   a) an elongated catheter shaft having an outer diameter and an inner lumen therein adapted to pass inflation fluid therethrough;
   b) an inflatable member on a distal portion of the catheter shaft having proximal and distal skirts and an interior in fluid communication with the inner lumen of the catheter shaft and having an operating inflated diameter of between 15-50 mm;
   c) means to reinforce the catheter shaft to prevent significant extension or failure of the catheter shaft or the juncture between the catheter shaft and the inflatable member when the inflatable member is inflated to dilate a prostatic urethra within a patient;
   d) means connected to the catheter shaft to direct inflation fluid through the inner lumen in the catheter shaft to the interior or the inflatable member;
   e) wherein the means to reinforce the catheter shaft is an elongated core member disposed within the inner lumen of the catheter shaft having a distal extremity secured to a distal portion of the catheter shaft and having a proximal extremity secured to a proximal portion of the catheter shaft; and
   f) wherein the distal extremity of the elongated core is secured to the distal portion of the catheter shaft at a location adjacent the proximal end of the inflatable member.

5. The catheter of claim 4 wherein the core member is secured to a high strength tubular member which is secured within the inner lumen of the catheter shaft at a location adjacent the proximal skirt of the inflatable member.

6. The catheter of claim 5 wherein the high strength tubular member is formed of stainless steel.

7. The catheter of claim 4 wherein the means to reinforce the catheter shaft is one or more elongated high strength members disposed within a wall of the catheter shaft.

8. The catheter of claim 7 wherein the elongated high strength members are ribbon-shaped.

9. The catheter of claim 8 wherein the elongated high strength members are formed of stainless steel.

10. The catheter of claim 4 wherein the catheter shaft extends through the interior of the inflatable member, is secured to proximal and distal skirts of the inflatable member and is provided with means to increase the length of the inflatable member upon the deflation thereof.

11. The catheter of claim 4 wherein the proximal skirt of the inflatable member is secured to the exterior of a tubular element having a flared distal end which in turn is secured to the catheter shaft.

12. The catheter of claim 4 wherein the distal skirt of the inflatable member is secured to the exterior of a tubular element having a flared proximal end which in turn is secured to the catheter shaft.

13. The catheter of claim 4 wherein the inflatable member has an effective deflated profile of less than about 5 mm.

14. A catheter for dilating a prostatic urethra comprising:
   a) an elongated catheter shaft having an outer diameter and an inner lumen therein adapted to pass inflation fluid therethrough;
   b) an inflatable member secured to a distal portion of the catheter shaft having proximal and distal skirts and a maximum inflated diameter between 15-50 mm;
   c) extendable means disposed within the interior of the inflatable member to increase the distance between the ends of the inflatable member upon the deflation thereof in order to reduce the deflated profile thereof; and
   d) wherein said extendable means includes interfitting portions with a proximal portion being secured to the proximal skirt of the balloon, with a distal portion being secured to the distal skirt of the balloon and with a biasing means for urging one of the interfitting portions to move relative to the outer portion.

15. The balloon catheter of claim 14 wherein the biasing means is a coiled spring disposed within said inner lumen of said catheter shaft.

16. The balloon catheter of claim 14 wherein the biasing means is at least one leaf spring having a distal end secured to one of the interfitting portions and a proximal end secured to the other interfitting portion.

17. The balloon catheter of claim 14 wherein reinforcing means is disposed within the catheter shaft to prevent significant extensions or failure of the catheter shaft when the inflatable member is inflated to dilate a prostatic urethra within a patient.

18. A catheter for dilating a prostatic urethra comprising:
   a) an elongated catheter shaft having an outer diameter and an inner lumen therein adapted to pass inflation fluid therethrough;
   b) an inflatable member on a distal portion of the catheter shaft having proximal and distal ends and a maximum inflated diameter at least about 15 mm; and
   c) a reinforcing member extending from a proximal portion of the catheter shaft to at least the proximal end of the inflatable member which allows the catheter to be subjected to a tensile force of at least 10 pounds without significant extension or failure thereof.

* * * * *